United States Patent
Maeda et al.

(10) Patent No.: US 7,407,507 B2
(45) Date of Patent: Aug. 5, 2008

(54) BALLOON CATHETER SUITED TO KISSING TECHNIQUES

(75) Inventors: Yasushi Maeda, Osaka (JP); Masao Horie, Osaka (JP)

(73) Assignee: Nipro Corporation, Osaka (JP)

( * ) Notice: Subject to any disclaimer, the term of this patent is extended or adjusted under 35 U.S.C. 154(b) by 755 days.

(21) Appl. No.: 10/868,937

(22) Filed: Jun. 17, 2004

(65) Prior Publication Data

US 2004/0260330 A1    Dec. 23, 2004

(30) Foreign Application Priority Data

Jun. 18, 2003    (JP) ............................. 2003-173902

(51) Int. Cl.
*A61M 29/00* (2006.01)
(52) U.S. Cl. .................................... 606/194
(58) Field of Classification Search ................. 606/92, 606/94, 191, 192, 194; 604/96.01, 103.14, 604/103.08, 103.13
See application file for complete search history.

(56) References Cited

U.S. PATENT DOCUMENTS 4,896,670 A  *  1/1990  Crittenden ................. 606/194
5,503,631 A      4/1996  Onishi et al. ................ 604/96
6,306,144 B1    10/2001  Sydney et al. .............. 606/108
2002/0038103 A1  3/2002  Estrada et al. ......... 604/103.09

FOREIGN PATENT DOCUMENTS

| EP | 0 693 293 A1 | 1/1996 |
|---|---|---|
| JP | 10-216220 A | 8/1998 |
| WO | 00/67828 A1 | 11/2000 |
| WO | 01/76525 A2 | 10/2001 |
| WO | 2004/043532 A1 | 5/2004 |

* cited by examiner

*Primary Examiner*—Nicholas D. Lucchesi
*Assistant Examiner*—Theodore J Stigell
(74) *Attorney, Agent, or Firm*—Kubovcik & Kubovcik

(57) ABSTRACT

A balloon catheter which is good in cross ability and is also good in gripping property so as not to cause slipping during kissing technique includes a tubular body having a balloon 3 provided in a distal section 12 of a shaft 1, the shaft 1 being flexible in the distal section 12 and stiff on its proximal side, whereby gripping property and cross ability are adjusted with good balance. Specifically, the gripping property is adjusted to 3.2 N to 6.0 N, and the cross ability is adjusted so that its initial value is not higher than 0.65 N and its middle value is 0.40 N.

15 Claims, 7 Drawing Sheets

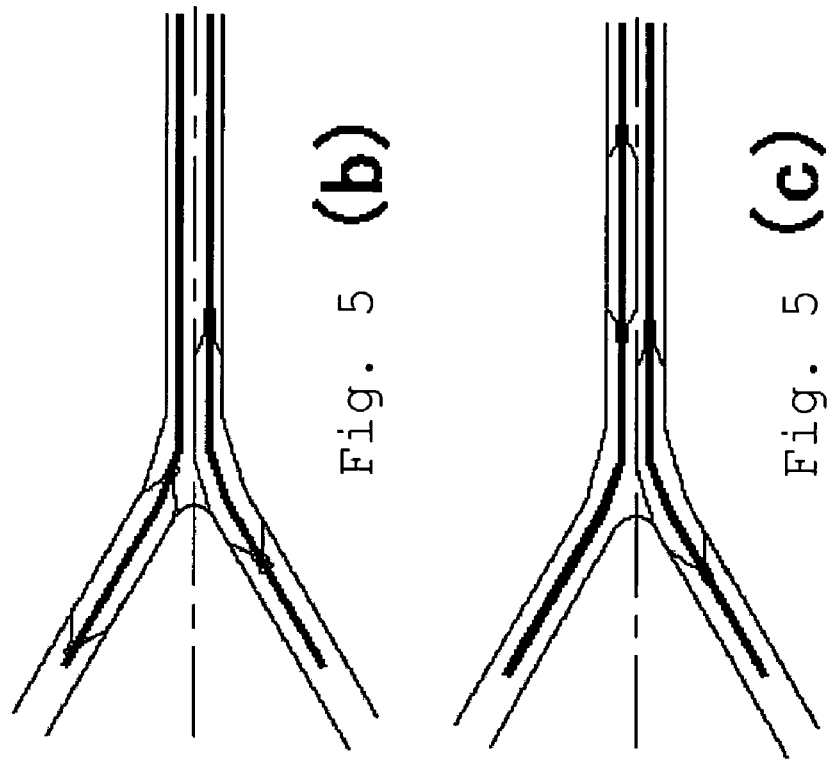
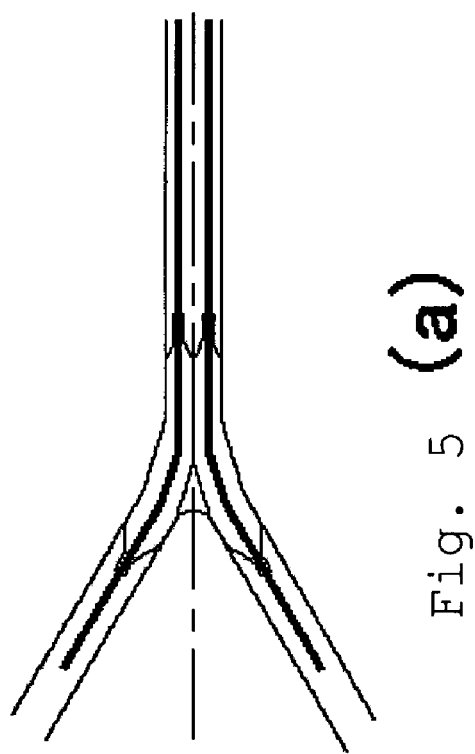
Fig. 5 (a)
Fig. 5 (b)
Fig. 5 (c)

BALLOON CATHETER SUITED TO KISSING TECHNIQUES

FIELD OF THE INVENTION

The present invention relates to a balloon catheter. The balloon catheter according to the present invention is particularly suited to treatment of an area, such as a bifurcation of a blood vessel, which requires an operation of inserting two balloon catheters and expanding them in an objective area at the same time (also called a kissing technique).

BACKGROUND OF THE INVENTION

Balloon catheters have heretofore been used for treatment of stenoses due to thrombi formed in organic lumina of blood vessels, bile ducts, air tubes and other organs.

A balloon catheter has a form approximately as shown in FIG. 1, and having a guide wire (GW) inserted through its internal cavity from a guide wire port 11, where the guide wire (GW) is inserted into, for example, a blood vessel. A balloon catheter (BC) is required to have an ability to cross to an objective area (cross ability), and therefore, is required to have an ability to be pushed into an objective area along the guide wire (GW) (pushability), followability which allows the balloon catheter (BC) to be easily deformed along the guide wire (GW), and a lubricative property of a portion to be inserted. To improve the pushability and the followability, a shaft 1 of the balloon catheter (BC) in general is flexible in a distal section 12 on a distal side relative to the guide wire port 11 and is stiff on a proximal side relative to the same. In addition, to improve the cross ability, a lubricative property is imparted by lubrication processing to the distal section 12 on the distal side relative to the guide wire port 11, which section includes the balloon 3 and a distal portion 2 extending from the balloon straight portion toward the distal end. As a method for lubrication processing, in general, the formation of a lubricant film by silicone coating or hydrophilization processing with polyvinylpyrrolidone (PVP) or the like is adopted (U.S. Pat. Nos. 5,503,631 and U.S. Pat. No. 6,306,144). In FIG. 1, reference numeral 36 denotes a marker for confirming the position of the inserted balloon 3.

There is a case where stenoses occur in both bifurcated blood vessels in the vicinity of, for example, a bifurcation of a blood vessel. In this case, as shown in FIG. 4, two balloon catheters (BC and BC) are respectively inserted into areas which extend from the bifurcation to the bifurcated blood vessels, and balloons (B and B) are respectively expanded to perform treatment for expanding the stenoses (U.S. Pat. No. 4,896,670).

However, the operation (kissing techniques) of introducing two balloon catheters into a bifurcation of a blood vessel and inserting and expanding their respective balloons in areas which extend from the bifurcation to the bifurcated blood vessels has the problem that when the balloons are expanded, the mutually adjacent balloons slip together and one of the balloons moves and deviates from the objective area (see, FIGS. 5b: one slips toward the distal end, and 5c: one slips toward the proximal end) so that the balloon that has deviated from the objective area cannot accurately expand the stenosis (see, FIGS. 5a, 5b and 5c).

The present invention has been made in view of the above-mentioned problem, and an object of the invention is to provide a balloon catheter which is improved in cross ability and is also improved in stability in an objective area (gripping property), which properties are adjusted with good balance so as not to cause slipping during kissing techniques.

SUMMARY OF THE INVENTION

To solve the above-mentioned problem, the present inventors have conducted intensive research in pursuit of a balance of gripping property and cross ability on the basis of the fact that a higher cross ability produces higher reachability to objective areas but a higher gripping property produces lower cross ability, and have discovered that if the gripping property is adjusted to an appropriate value, a balloon can be guided to an objective area and, in addition, is prevented from moving and deviating from the objective area during kissing techniques, and have completed the invention. Namely, the invention relates to a balloon catheter suited to kissing techniques which includes a tubular body having a balloon provided on a flexible distal section of a stiff shaft and has a gripping property and a cross ability adjusted with good balance.

The term "cross ability" usually refers to the ability of the catheter to successfully transmit pushing and guiding and steering forces applied at the proximal hub by the physician, such that the distal tip of the balloon catheter pushes into, through and past a constricted lesion. The term "gripping property" means the stability that the balloon catheter achieves in the objective area. The term "pushability" means a transmission of longitudinal forces along the guidewire from its proximal end to its distal end. The term "followability" means an easily deformable property of the balloon catheter along the guidewire.

Specifically, for example, the gripping property is expressed by a resistance value which is obtained when a balloon having a length of 20 mm and a folding diameter of 0.70 to 0.90 mm is fitted into a polyurethane tube (a polyether based aliphatic thermoplastic urethane under the trademark TELOCOFLEX EG-80A by Thermomedics, Inc.) having an inner diameter of 2.4 mm and an outer diameter of 4.0 mm and a length of 10 mm and the balloon is expanded to a diameter of 2.5 mm and pulled toward a proximal side at a speed of 250 mm/min in a water bath of 37° C., the resistance value being measured by a Universal Tensile Testing Instrument, ORIENTEC RTC-1225A (see, FIG. 6).

The cross ability is expressed by a resistance value which is obtained when a balloon having a length of 20 mm and a folding diameter of 0.70 to 0.90 mm is pushed and inserted into a hole having a diameter of 0.4 mm in a polyurethane film (Esmer URS, Nippon Matai) having a thickness of 1 mm along a guidewire at a speed of 500 mm/min in a water bath of 37° C., the resistance value being measured by a Universal Tensile Testing Instrument, ORIENTEC RTC-1225A (see, FIG. 7).

The gripping property is adjusted to 3.2 N to 6.0 N, and the cross ability is adjusted so that its initial value is not higher than 0.65 N and its middle value is not higher than 0.40 N. Preferably, the gripping property is 4.0 N to 6.0 N, and the cross ability is adjusted so that its initial value is not higher than 0.50 N and its middle value is not higher than 0.39 N. The initial value means the resistance value exerted by the balloon tip when the balloon catheter is initially inserted into the polyurethane film, while the middle value means the resistance value exerted by the balloon straight portion following the tip insertion.

In the balloon catheter according to the invention, the balance of gripping property and cross ability depends on a forming material of the balloon and the state of its surface as well as a balance between the stiffness of the proximal side of the shaft and the flexibility of a distal section, and therefore, the balloon straight portion and a portion extending from the balloon straight portion on a distal side thereof generally are not subjected to lubrication. However, since the balloon catheter, first of all, needs to be made to reach an objective area, the distal portion extending from the balloon straight portion may also be subjected to lubrication processing in order to improve the cross ability, particularly the initial value of the cross ability, while maintaining the gripping property. As a method for lubricating the balloon, because of the ease of processing, a 5% or less solution of silicone in a flon solvent may be coated on the tip portion to form a silicone coating. In order to improve the cross ability while maintaining the gripping property, a 0.5% or less solution of silicone in flon solvent may also be coated on the balloon straight portion to form a silicone coating.

BRIEF DESCRIPTION OF THE DRAWINGS

FIG. 5 shows two balloon catheters in a bifurcation of a blood vessel wherein (a) is a normal state, (b) one balloon slips toward the distal end and (c) one balloon slips toward the proximal end.

THE MOST PREFERRED EMBODIMENTS OF THE INVENTION

An embodiment of the invention will be described below.

Figure 1:
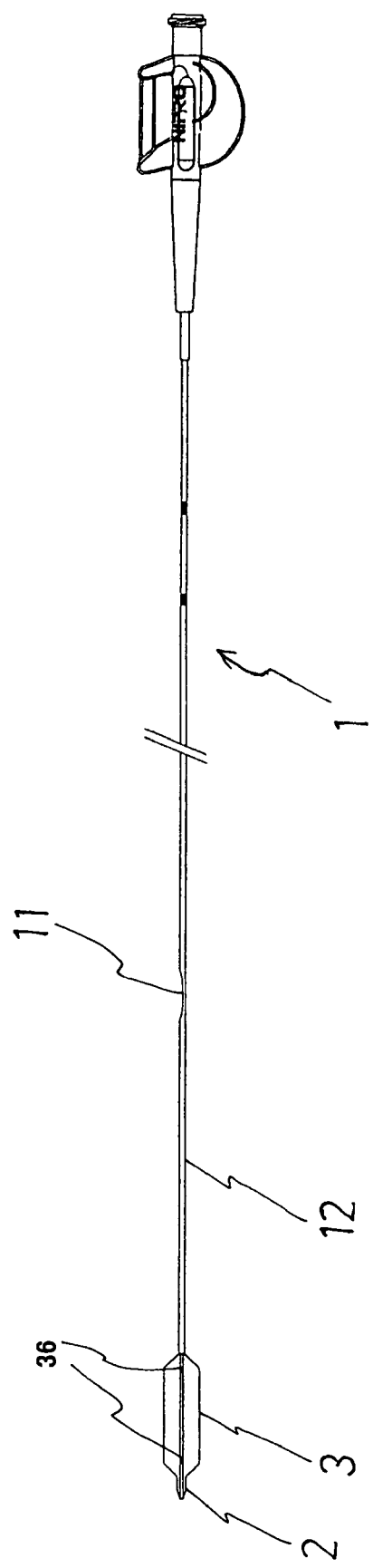
FIG. 1 is a view explaining a balloon catheter according to the invention.

A balloon catheter (BC) according to the invention, as shown in FIG. 1, includes a tubular body having a balloon 3 provided on a distal section 12 of a shaft 1, the shaft 1 being flexible in the distal section 12 and stiff on its proximal side relative to the distal section 12, whereby gripping property and cross ability are adjusted with good balance.

The balloon catheter is a catheter provided with an air-inflatable balloon 3 attached on the tip of the longitudinal flexible shaft 1, which is not limited to FIG. 1 but may have a well-known structure, and a lumen (outer lumen) communicating with an inner part of the balloon 3 to send air into the balloon 3 and remove the air from the expanded balloon 3, and another lumen (inner lumen) to transmit the guidewire which may have an optional structure known in the art of dilation catheters. One example of the balloon catheters used in the present invention is explained in detail using FIGS. 2 and 3.

The shaft 1 consists of a distal section, a transition section and a proximal section, in which the distal section 12 extending from the guidewire port 11 is about 200 mm to 300 mm and is flexible, and the proximal section extending from the guidewire port 11 is about 700 to 1400 mm and is stiff.

The distal section of the shaft 1 comprises double tubes composed of an inner tube 22 inside an outer tube 21 (FIG. 2 A-A' and FIG. 2 B-B'), in which the distal end of the outer tube 21 is jointed with a most proximal end 35 of the balloon 3, and the inner lumen of the outer tube 21 communicates with the inside of the balloon 3. The inner tube 22 extends from the jointed part between the outer tube 21 and the balloon 3 toward the distal section to penetrate through the inside of the balloon 3, and the most distal end 31 of the balloon 3 is jointed with the peripheral surface of the distal section of the inner tube 22. The outer tube 21 and the inner tube 22 are made from synthetic materials such as polyamide or polyamide elastomer, but the synthetic materials are not limited to these materials. The inner tube 22 terminates at the guidewire port 11 through which the guidewire (not shown) can be drawn away, and the guidewire port 11 is provided on the tubular wall of the tube 21 (FIG. 2 C-C').

Figure 2:
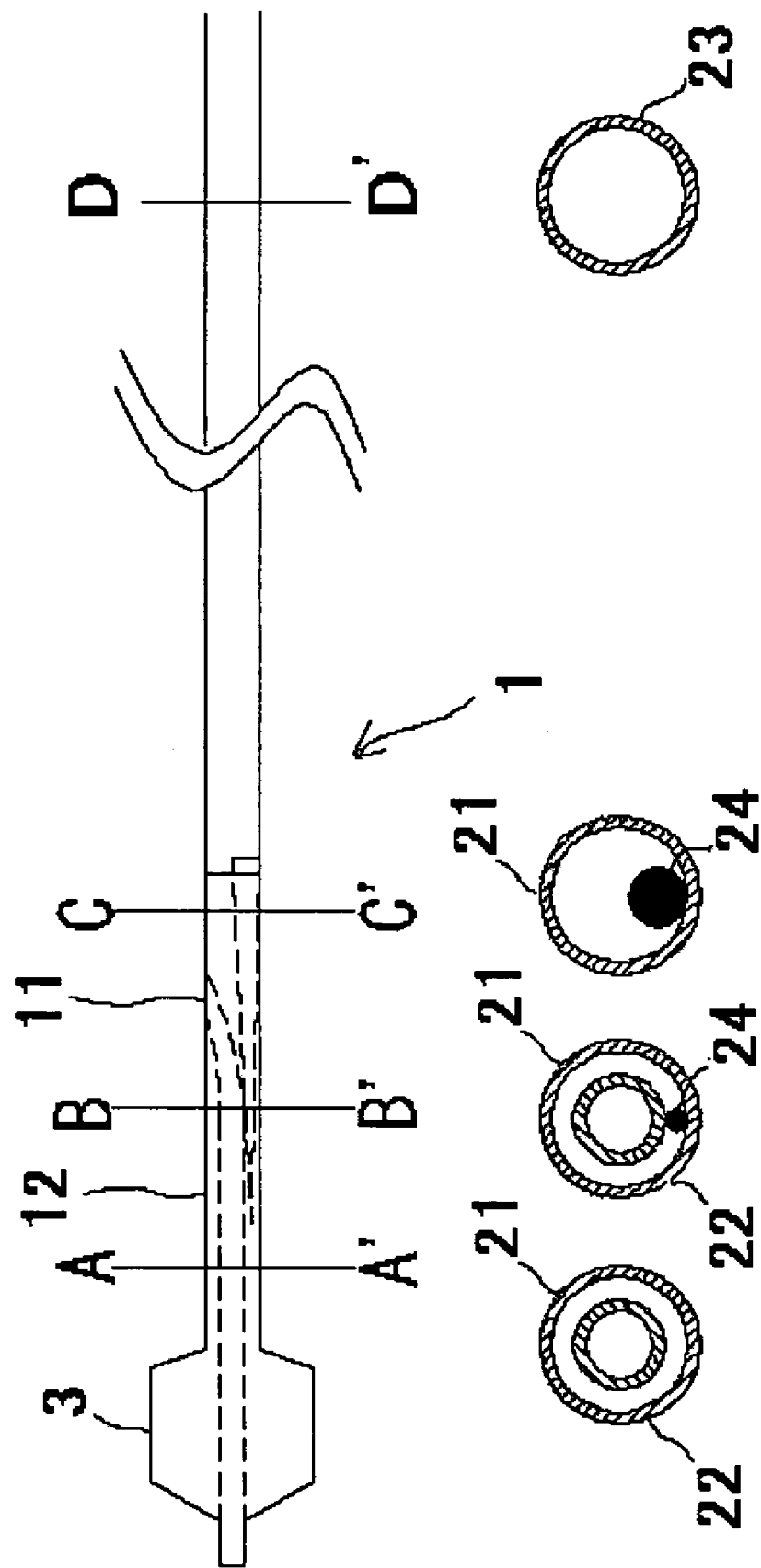
FIG. 2 is a cross-sectional view of a balloon catheter.

The proximal section of the shaft 1 is a single tube 23 forming a stiff proximal section connected with the outer tube 21, and is composed of a metallic material such as stainless steel, SUS 304, polyimide or polyetherketone (FIG. 2 D-D').

The transition section of the shaft 1 comprises a portion of the proximal section and of the distal section of the shaft in which a core wire 24 is inserted. The core wire 24 is made of a metallic material such as SUS 304 and is inserted in the proximal section of the outer tube 21 and the distal section of the outer tube 23 (FIG. 2, B-B' and C-C', black circle) to alleviate a large change of the stiffness between the outer tube 21 and the outer tube 23.

Figure 3:
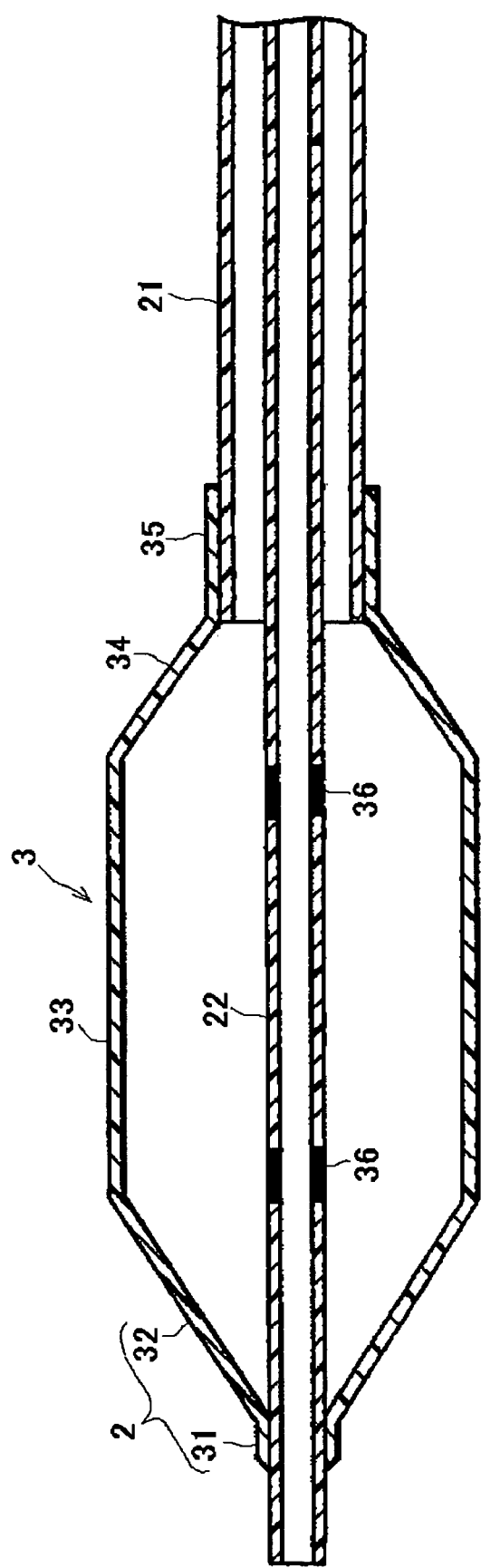
FIG. 3 is a cross-sectional view of a balloon provided on the shaft.
Figure 4:
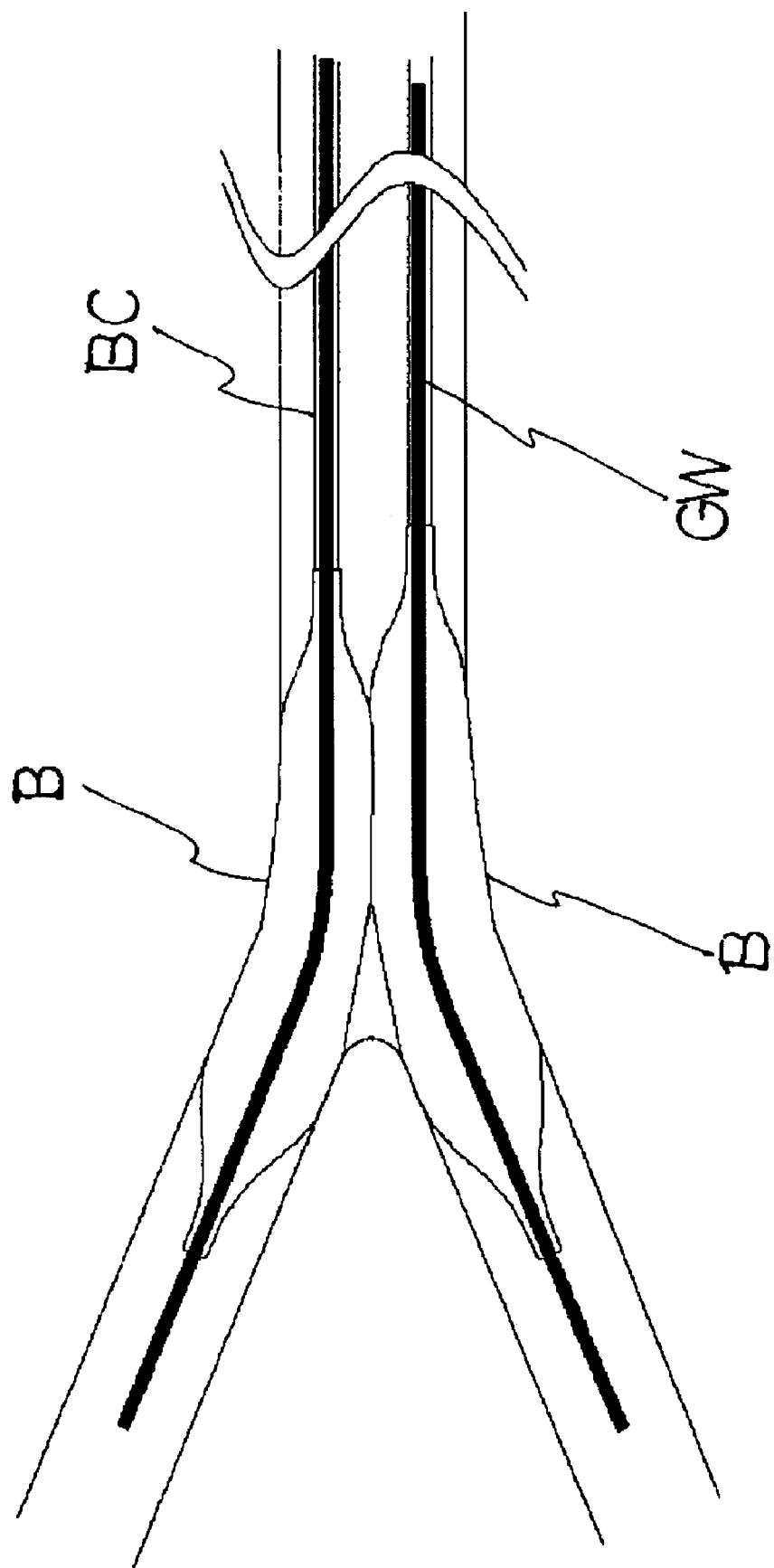
FIG. 4 is an explanatory view of a kissing technique wherein B is a balloon, BC is a balloon catheter and GW is a guidewire.
Figure 6:
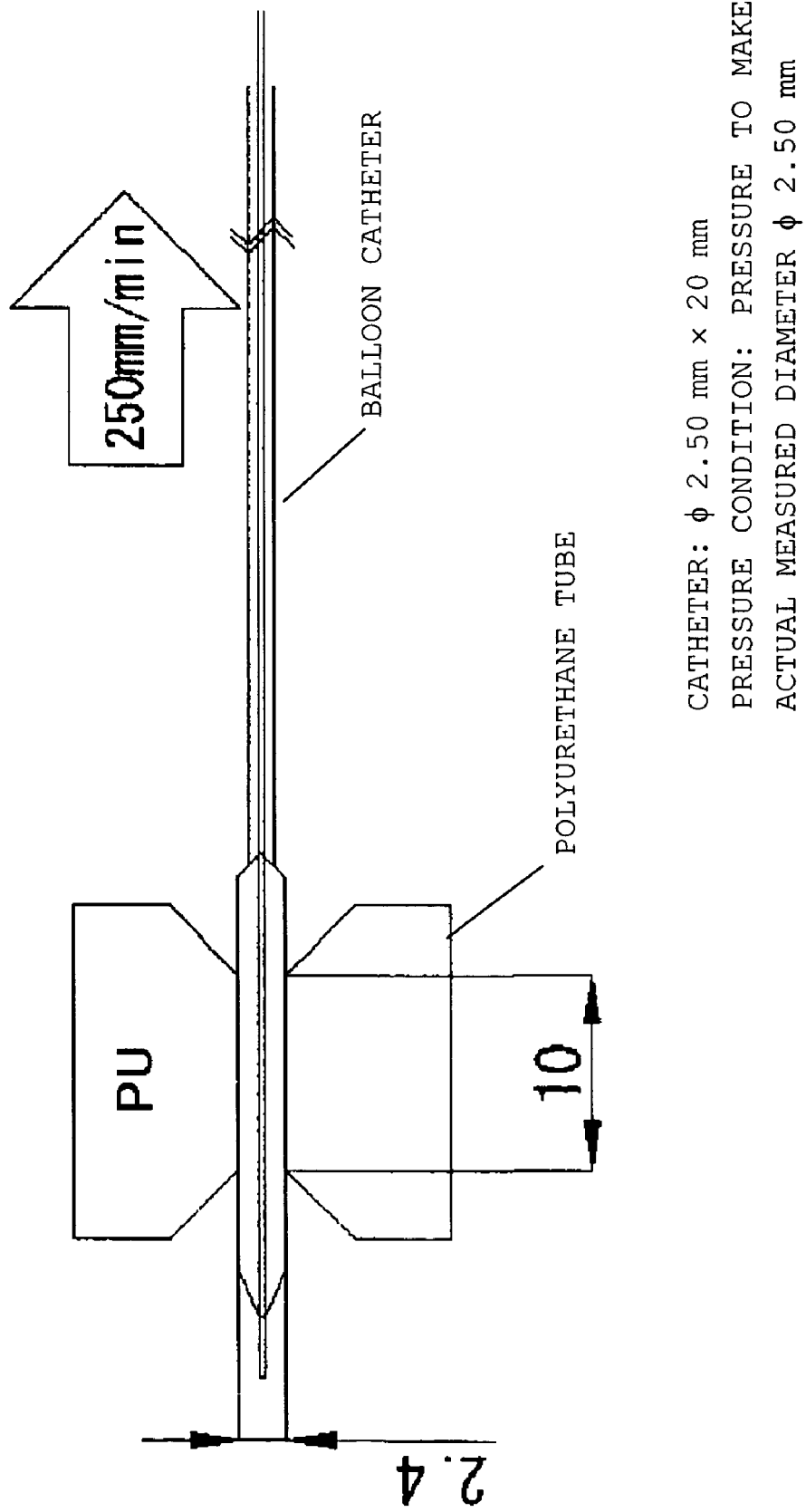
FIG. 6: A view showing a method of measuring the gripping property of a balloon catheter.
Figure 7:
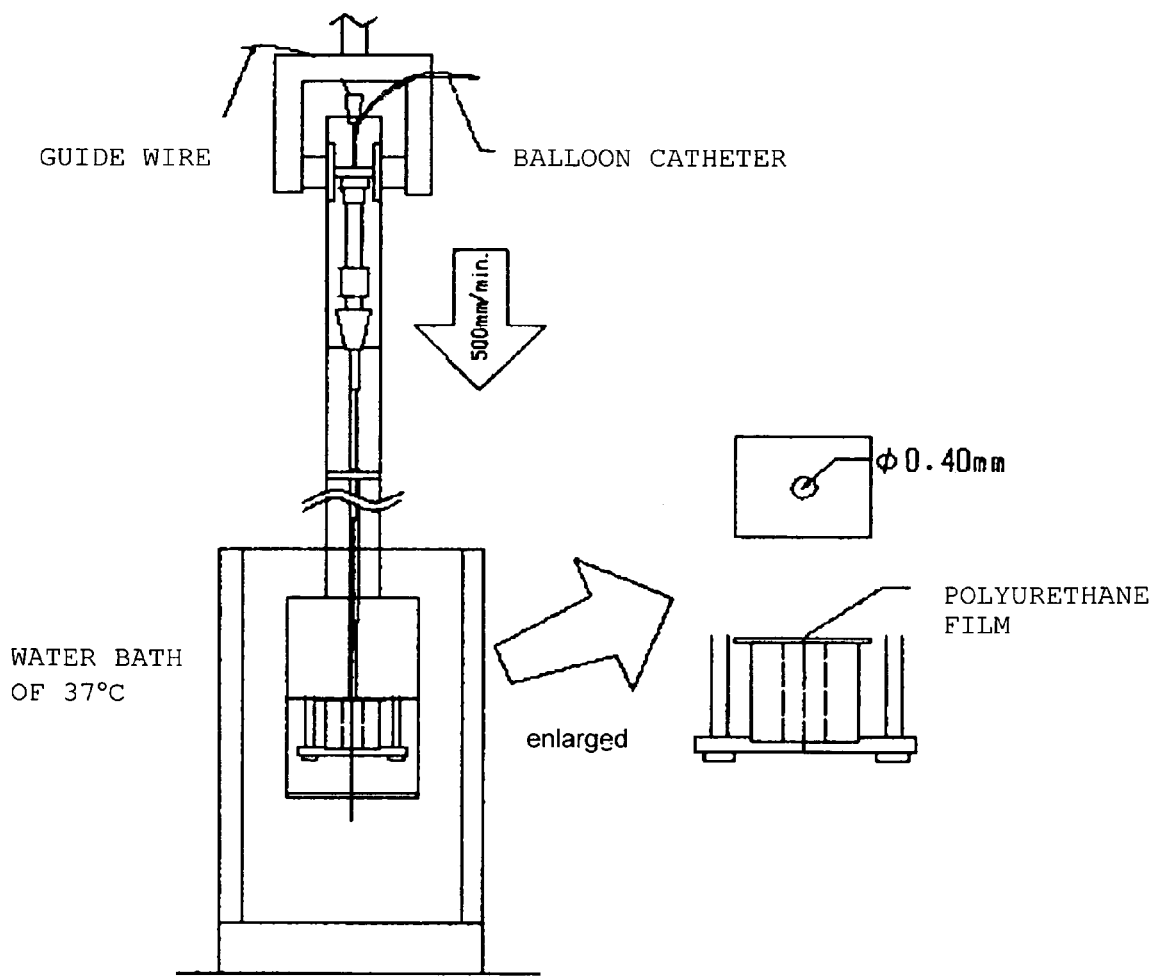
FIG. 7: A view showing a method of measuring the cross ability of a balloon catheter.

The balloon 3 in the present invention consists of the balloon most distal portion (distal end) 31, the distal tapered portion 32, the balloon straight portion 33, the proximal tapered portion 34 and the most proximal portion 35 (proximal end) (FIG. 3). The distal end portion 2 extending from the balloon straight portion 33 toward the distal side refers to the most distal end portion (distal end) 31 and the distal tapered portion 32.

The balloon in the present invention is a balloon for medical instruments which is a given length of tube made of polymer materials and can be expanded in a radial direction under pressure.

The polymer materials in the balloon 3 include synthetic elastomers such as polyamide elastomer, polyester elastomer, polyurethane elastomer and the like, and polyamide elastomers include polyamide/polyether block copolymer, polyamide/polyester block copolymer and the like. The polyamide/polyether block copolymer consists of two or more hard segments of polyamide and two or more soft segments of polyether. The polyamide hard segments in the polyamide/polyether block copolymer are polyamide consisting of C6 or more higher carboxylic acids and C6 or more higher organic diamines, or C6 or more higher aliphatic ω-amino acids, and the polyether soft segments consisting of C2 to C10 diols. The polyamide/polyether block copolymer has an elasticity of 150,000 psi ($1.034 \times 10^9$ Pa) or less, preferably, 50,000 to 120,000 psi ($3.448 \times 10^8$ to $8.274 \times 10^8$ Pa), a hardness of Shore D 60 or more, preferably, 65 to 75, and includes the polyamide hard segments in an amount of 50% to 95% by weight, preferably, 80 to 90% by weight (based on the polyamide/polyether block copolymer).

The polyamide segments and polyether segments have repeated segments of 5 to 10, in which the polyamide segments may be selected from the group consisting of nylon 12, nylon 11, nylon 9, nylon 6, nylon 6/12, nylon 6/11, nylon 6/9 and nylon 6/6. The polyether segments may be selected from the group consisting of polyethylene glycol, polypropylene glycol, poly(tetramethylene ether), poly(pentamethylene ether) and poly(hexamethylene glycol).

The polyamide/polyether block copolymers are sold commercially under the PEBAX trademark by Atofina, Japan, or Atomchem North America, Inc. Examples of suitable commercially available polymers are the Pebax 33 series polymers with a hardness of 60 and above (Shore D scale) especially, Pebax 7033 and 6333. Pebax 7033 includes 90 parts by weight of nylon 12 segments and 10 parts by weight of poly(tetramethylene ether) segments. Pebax 6333 includes 80 parts by weight of nylon 12 segments and 20 parts by weight of poly(tetramethylene ether) segments.

The balloon 3 in the present invention consists of the balloon most distal portion (distal end) 31, the distal tapered portion 32, the balloon straight portion 33, the proximal tapered portion 34 and the most proximal portion (proximal end) (FIG. 3). The most distal portion 31 has a diameter of 0.4 to 0.7 mm and a length of 2 to 6 mm and the balloon straight portion 33 has a diameter of 0.8 to 7.0 mm and a length of 5 to 40 mm. A diameter of the most proximal portion is not limited in the present invention. The distal tapered portion 32 and the proximal tapered portion 34 are tapered portions from the most distal portion 31 to the balloon straight portion 33, and from the balloon straight portion 33 to the proximal portion 35, respectively. The thickness of the balloon is 15 to 40 μm and the highest dilation ratio of the balloon straight portion is 4 to 8 times.

The lubrication processing refers to film-formation by application of a silicon solution, or hydrophilization processing by applying a hydrophilic polymer solution, such as polyvinylpyrrolidone solution.

The distal portion 2 and the balloon straight portion 33 in the balloon in the present invention include the following embodiments:

(i) the most distal end portion, the distal tapered portion and the balloon straight portion are not subjected to lubrication processing; (Ex.1)

(ii) the most distal end portion and the distal tapered portion are subjected to lubrication processing while the balloon straight portion is not subjected to lubrication processing;

(a) the most distal end and the distal tapered portion have a polyvinylpyrrolidone coating while the balloon straight portion is not subjected to lubrication processing; (Ex. 3)

(b) the most distal end portion and the distal tapered portion have a silicone coating by applying a 5% or less silicone solution thereon while the balloon straight portion is not subjected to lubrication processing. (Ex. 4-6)

(iii) the most distal end portion, the distal tapered portion and the balloon straight portion are subjected to lubrication processing;

(a) the most distal end portion, the distal tapered portion and the balloon straight portion are subjected to lubrication processing, and the most distal end portion and the distal tapered portion have a silicone coating by applying a 5% or less silicone solution thereon and the balloon straight portion has a silicone coating by applying a 0.5% or less silicone solution thereon; (Exs. 7-9)

(b) the most distal end portion, the distal tapered portion and the balloon straight portion are subjected to lubrication processing, and the most distal end portion and the distal tapered portion have a polyvinylpyrrolidone coating by applying a polyvinylpyrrolidone solution thereon and the balloon straight portion has a silicone coating by applying a 0.5% or less silicone solution thereon; (Ex.10) and (iv) the most distal end portion and the distal tapered portion are not subjected to lubrication processing while the balloon straight portion has a silicone coating by applying a 0.5% or less silicone solution thereon. (Ex.2)

The silicone useful in the present invention includes dimethylsilicone, MXD4 or DC-360 manufactured by Dow Corning, and the solvent includes flon, heptane and the like.

The hydrophilic polymer useful in the present invention includes polyvinylpyrrolidones such as poly(vinylpyrrolidone) homopolymer and poly(vinylpyrrolidone) copolymer, and polyalkylene glycols such as polyethylene glycol, alkoxy polyalkylene glycol.

The useful solvent for the hydrophilic polymer includes polar solvents such as alcohols, glycols and water; aliphatic hydrocarbons such as heptane and hexane; aromatic hydrocarbons such as toluene and xylene; chlorinated hydrocarbons such as perchloroethylene, methylene chloride, chloroform, carbon tetrachloride, and 1,1,1-trichloroethane; and fluorinated carbons.

A 5% or less solution, preferably, a 5% to 10% solution of the hydrophilic polymer is used for hydrophilic processing. The method for coating the most distal portion, the distal tapered portion and the balloon straight portion in the balloon with the silicone solution or the hydrophilic polymer solution includes dipping, coating, spraying and the like. The coating thickness after evaporating the solvent is 1 to 10 μm, preferably, 2 to 6 μm, and most preferably, 2 to 4 μm. The solvent may be evaporated at an ambient temperature.

The gripping property represents an ability to prevent slipping from easily occurring, namely, stability in an objective area, in the case where a balloon guided to an objective area moves by slipping when the balloon is expanded during treatment using kissing techniques or treatment of in-stent restenosis (restenosis occurring in a stent). In the invention, gripping property is expressed by a resistance value which is obtained when a balloon of a length of 20 mm and a folding diameter of 0.7 mm is fitted into a polyurethane tube of diameter 2.4 mm and length 10 mm and the balloon is expanded to a diameter of 2.5 mm and pulled toward a proximal side at a speed of 250 mm/min in a water bath of 37° C. The cross ability represents an ability to pass through to an objective area and is expressed by a resistance value which is obtained when a balloon of length 20 mm and folding diameter 0.7 mm which is expanded to a diameter of 2.5 mm is pushed and inserted into a hole of a polyurethane film having a thickness of 1 mm and a hole diameter of 0.4 mm at a speed of 500 mm/min in a water bath of 37° C. Since better gripping property produces low cross ability, in the invention, both are adjusted with good balance.

Namely, in the invention, the gripping property is adjusted to 3.2 N to 6.0 N, and the cross ability is adjusted so that its initial value (when the balloon starts to be inserted) is not higher than 0.65 N and its middle value is not higher than 0.40 N. Preferably, the gripping property is 4.0 N to 6.0 N, and the cross ability is adjusted so that its initial value is not higher than 0.50 N and its middle value is not higher than 0.39 N. When the gripping property is less than 3.2 N, there is a risk that the balloon deviates from the bifurcated part during kissing, whereas when the gripping property is higher than 6.0 N, the cross ability becomes inferior and there is a case where the catheter becomes difficult to insert into an objective area.

In the balloon catheter according to the invention, the balance of gripping property and cross ability depends on its forming materials and the states of its surfaces as well as the balance between the stiffness of the proximal side of the shaft 1 and the flexibility of the distal section 12, and therefore, the balloon straight portion 33 and the distal portion 2 extending from the balloon straight portion 33 on a distal side (the most distal portion 31 and the distal tapered portion 32) generally are not subjected to lubrication processing. However, the distal portion 2 extending from the balloon straight portion 33 may also be subjected to lubrication processing in order to improve the cross ability, particularly the initial value of the cross ability, while maintaining the gripping property, and as a method for lubrication processing, because of the ease of processing, a 5% or less silicone solution using flon as a solvent may be coated to form a film of silicone (lubricant). Alternatively, a 1% polyvinylpyrrolidone solution using chloroform as solvent may also be coated on the distal portion. In order to improve the cross ability while maintaining the gripping property, a 0.5% or less silicone solution using flon as a solvent may also be coated to form a film of silicone on the balloon.

Manufacturing Method

A balloon 3 having a folding diameter of 0.74 mm and a thickness of 20 μm was formed by melting and extruding a polyamide/polyether block copolymer (PEBAX 7033 manufactured by Atofina Japan) into a balloon. The lengths of the balloon portions respectively are as follows: the most distal portion 31, 3 mm; the distal tapered portion 32, 4 mm; the straight portion 33, 20 mm; the proximal tapered portion 34, 3 mm and the most proximal portion 35, 2 mm. The inside of the most distal portion 31 in the balloon 3 was jointed to the peripheral surface of the polyamide inner tube 22 at the distal end, and the inside of the most proximal portion 35 in the balloon 3 was jointed to the peripheral surface of the polyamide outer tube 21 at the distal end to form the balloon catheter. The polyamide/polyether block copolymer (PEBAX 7033) has a Shore D hardness of 69, a flexural modulus of 67,000, an ultimate tensile strength of 8,300 psi, and an ultimate elongation of 400%.

The various concentrations of silicone solution in flon shown in Table 1 or a 1% polyvinylpyrrolidone solution in chloroform (hydrophilization processing *2) were applied on the most distal portion 31 and the distal tapered portion 32 (distal portion 2), and a 0.5% silicone solution in flon was applied on the balloon straight portion 33.

For the comparison to the present invention, polyamide 12, or a blend of polyamide 12 and polyamide/polyether block copolymer (PEBAX 5533, Shore D hardness 55, manufactured by Atofina Japan, blend ratio 90/10 by weight) was used for making a balloon (Comparative Examples 3 to 5). Further, for the comparison, commercially available balloon catheters were prepared (Comparative Examples 1, 2 and 4 to 9). Pebax 7033 was used in Comparative Examples 10 and 11.

TEST EXAMPLES

As shown in Table 1, five balloon catheters each having a balloon of folding diameter 0.74 mm and a distal section of diameter 0.40 mm and length 3 mm were prepared and the gripping property and the cross ability of each of the balloon catheters were measured, whereby the results shown in Table 2 were obtained. A bifurcation model of a blood vessel (the distance from its insertion portion to its bifurcation: 200 mm, the length of the bifurcation: 30 mm) was fabricated from a polyurethane tube of diameter 2.4 mm, and this bifurcation model was used and two balloons were guided to the bifurcation in a water bath of 37° C. and a kissing technique was performed. The results shown in Table 2 were obtained.

It can be seen from Table 2 that if a balloon has a gripping property of not lower than 3.2 N, the balloon does not deviate, whereas if the cross ability resistance is not higher than 0.65 N in initial value and is not higher than 0.40 N in middle value, the balloon can be smoothly guided to an objective area. In terms of safety, it is preferable that the gripping property be 4.0-6.0 N and the cross ability resistance be not higher than 0.50 N in initial value and not higher than 0.39 N in middle value, because the gripping property and the cross ability are mutually inconsistent. In addition, it can also be seen that if a film of lubricant is formed on the tip portion 2, the cross ability is improved without causing slipping.

TABLE 1

|  | FORMING MATERIAL | LUBRICATING OF BALLOON STRAIGHT PORTION 33 | LUBRICATION OF DISTAL PORTION 2 |
| --- | --- | --- | --- |
| EMBODIMENT 1 | PEBAX 7033 | NO | NO |
| EMBODIMENT 2 | PEBAX 7033 | SILICONE (0.5%) | NO |
| EMBODIMENT 3 | PEBAX 7033 | NO | HYDROPHILIZATION PROCESSING *2 |
| EMBODIMENT 4 | PEBAX 7033 | NO | SILICONE (5%) |
| EMBODIMENT 5 | PEBAX 7033 | NO | SILICONE (1%) |
| EMBODIMENT 6 | PEBAX 7033 | NO | SILICONE (0.5%) |
| EMBODIMENT 7 | PEBAX 7033 | SILICONE (0.5%) | SILICONE (5%) |
| EMBODIMENT 8 | PEBAX 7033 | SILICONE (0.5%) | SILICONE (1%) |
| EMBODIMENT 9 | PEBAX 7033 | SILICONE (0.5%) | SILICONE (0.5%) |
| EMBODIMENT 10 | PEBAX 7033 | SILICONE (0.5%) | HYDROPHILIZATION PROCESSING *2 |
| COMPARATIVE EXAMPLE 1 | POLYAMIDE *1 | HYDROPHILIZATION PROCESSING | HYDROPHILIZATION PROCESSING |
| COMPARATIVE EXAMPLE 2 | POLYAMIDE ELASTOMER *1 | HYDROPHILIZATION PROCESSING | HYDROPHILIZATION PROCESSING |
| COMPARATIVE EXAMPLE 3 | BLEND (POLYAMIDE 12 and PEBAX 5533) | NO | NO |
| COMPARATIVE EXAMPLE 4 | BLEND (POLYAMIDE 12 and PEBAX 5533) | HYDROPHILIZATION PROCESSING *2 | NO |
| COMPARATIVE EXAMPLE 5 | BLEND (POLYAMIDE 12 and PEBAX 5533) | SILICONE (5%) | NO |
| COMPARATIVE EXAMPLE 6 | POLYAMIDE *1 | HYDROPHILIZATION PROCESSING | HYDROPHILIZATION PROCESSING |
| COMPARATIVE EXAMPLE 7 | POLYAMIDE ELASTOMER *1 | HYDROPHILIZATION PROCESSING | HYDROPHILIZATION PROCESSING |

TABLE 1-continued

|  | FORMING MATERIAL | LUBRICATING OF BALLOON STRAIGHT PORTION 33 | LUBRICATION OF DISTAL PORTION 2 |
|---|---|---|---|
| COMPARATIVE EXAMPLE 8 | POLYAMIDE ELASTOMER *1 | HYDROPHILIZATION PROCESSING | HYDROPHILIZATION PROCESSING |
| COMPARATIVE EXAMPLE 9 | POLYAMIDE ELASTOMER *1 | HYDROPHILIZATION PROCESSING | HYDROPHILIZATION PROCESSING |
| COMPARATIVE EXAMPLE 10 | PEBAX 7033 | SILICONE (1%) | NO |
| COMPARATIVE EXAMPLE 11 | PEBAX 7033 | SILICONE (1%) | SILICONE (1%) |

(Note 1) Comparative Examples 1 and 2 as well as Comparative Examples 6 to 9 are commercially marketed products.
(Note 2) The folding diameter of the balloon of each of Comparative Examples 1 to 3 and 6 to 9 differs from the folding diameter of the balloon of each of the embodiments of the invention, and the folding diameters of those respective balloons are 0.72 mm, 0.71 mm, and 0.81 mm, 0.77 mm, 0.84 mm, 0.76 mm, and 0.79 mm.

Examples 6 to 9 are commercially marketed products.
(Note 2) The folding diameter of the balloon of each of Comparative Examples 1 to 3 and 6 to 9 differs from the folding diameter of the balloon of each of the embodiments of the invention, and the folding diameters of those respective balloons are 0.72 mm, 0.71 mm, 0.81 mm, 0.77 mm, 0.84 mm, 0.76 mm and 0.79 mm.

TABLE 2

|  | CROSS ABILITY (INITIAL VALUE) | CROSS ABILITY (MIDDLE VALUE) | GRIPPING PROPERTY | OCCURRENCE OF SLIPPING *1 | GUIDE TO OBJECTIVE AREA |
|---|---|---|---|---|---|
| EMBODIMENT 1 | 0.61 N | 0.38 N | 5.5 N | 0/5 | SMOOTH |
| EMBODIMENT 2 | 0.57 | 0.36 | 3.4 | 0/5 | SMOOTH |
| EMBODIMENT 3 | 0.45 | 0.38 | 4.3 | 0/5 | SMOOTH |
| EMBODIMENT 4 | 0.48 | 0.38 | 4.2 | 0/5 | SMOOTH |
| EMBODIMENT 5 | 0.47 | 0.37 | 4.5 | 0/5 | SMOOTH |
| EMBODIMENT 6 | 0.48 | 0.39 | 4.6 | 0/5 | SMOOTH |
| EMBODIMENT 7 | 0.49 | 0.35 | 3.3 | 0/5 | SMOOTH |
| EMBODIMENT 8 | 0.50 | 0.35 | 3.3 | 0/5 | SMOOTH |
| EMBODIMENT 9 | 0.49 | 0.36 | 3.4 | 0/5 | SMOOTH |
| EMBODIMENT 10 | 0.43 | 0.34 | 3.2 | 0/5 | SMOOTH |
| COMPARATIVE EXAMPLE 1 | 0.49 | 0.29 | 1.8 | 5/5 | SMOOTH |
| COMPARATIVE EXAMPLE 2 | 0.39 | 0.17 | 2.1 | 5/5 | VERY SMOOTH |
| COMPARATIVE EXAMPLE 3 | 0.74 | 0.39 | 3.4 | 0/5 | DIFFICULT |
| COMPARATIVE EXAMPLE 4 | 0.44 | 0.20 | 1.6 | 5/5 | VERY SMOOTH |
| COMPARATIVE EXAMPLE 5 | 0.47 | 0.32 | 2.1 | 5/5 | SMOOTH |
| COMPARATIVE EXAMPLE 6 | 0.54 | 0.39 | 1.9 | 5/5 | SMOOTH |
| COMPARATIVE EXAMPLE 7 | 0.68 | 0.44 | 1.9 | 5/5 | DIFFICULT |
| COMPARATIVE EXAMPLE 8 | 0.54 | 0.28 | 1.8 | 5/5 | SMOOTH |
| COMPARATIVE EXAMPLE 9 | 0.53 | 0.31 | 2.1 | 5/5 | SMOOTH |
| COMPARATIVE EXAMPLE 10 | 0.52 | 0.34 | 2.9 | 2/5 | SMOOTH |
| COMPARATIVE EXAMPLE 11 | 0.48 | 0.36 | 3.1 | 2/5 | SMOOTH |

*1: Number of slipped samples/total number of samples

As is apparent from the foregoing description, with the balloon catheter according to the invention it is possible to perform treatment of a bifurcation safely and reliably, because the balloon catheter has a high ability to cross to an objective area and causes no slipping during kissing during treatment of a stenosis formed in a bifurcation of a blood vessel.

What is claimed is:

1. A balloon catheter suited to kissing techniques which comprises a tubular body having a balloon provided on a flexible distal section of a shaft, the balloon comprising a most distal end portion, a distal tapered portion, a balloon straight portion, a proximal tapered portion and a most proximal end portion, the shaft comprising a flexible distal section, a transient section and a stiff proximal section, wherein the balloon catheter has (1) a gripping property of 3.2 N to 6.0 N, which is obtained when a balloon having a length of 20 mm and a folding diameter of 0.70 to 0.90 mm is fitted into a polyurethane tube having a diameter of 2.4 mm and a length of 10 mm and the balloon is expanded to a diameter of 2.5 mm and pulled toward a proximal side of said tube at a speed of 250 mm/min in a water bath of 37° C.; and (2) a cross ability of not higher than 0.65 N for the most distal end portion and of not higher than 0.40 N for the straight portion, which values are obtained when a balloon having a length of 20 mm and a folding diameter of 0.70 to 0.90 mm which is expanded to a diameter of 2.5 mm is pushed and inserted into a hole having a diameter of 0.4 mm in a polyurethane film having a thickness of 1 mm at a speed of 500 mm/min in a water bath of 37° C.

2. The balloon catheter according to claim 1, wherein the gripping property is 4.0 N to 6.0 N and the cross ability is not higher than 0.50 N for the most distal end portion and not higher than 0.39 N for the straight portion.

3. The balloon catheter according to claim 1, wherein the balloon straight portion is not lubricated or has a silicone coating formed by applying a 0.5% or less silicone solution thereon.

4. The balloon catheter according to claim 1, wherein the most distal end portion, the distal tapered portion and the balloon straight portion are not lubricated.

5. The balloon catheter according to claim 1, wherein the most distal end portion and the distal tapered portion are lubricated while the balloon straight portion is not lubricated.

6. The balloon catheter according to claim 1, wherein the most distal end and the distal tapered portion have a polyvinylpyrrolidone coating while the balloon straight portion is not lubricated.

7. The balloon catheter according to claim 1, wherein the most distal end portion and the distal tapered portion have a silicone coating formed by applying a 5% or less silicone solution thereon while the balloon straight portion is not lubricated.

8. The balloon catheter according to claim 1, wherein the most distal end portion, the distal tapered portion and the balloon straight portion are lubricated, and the most distal end portion and the distal tapered portion have a silicone coating formed by applying a 5% or less silicone solution thereon and the balloon straight portion has a silicone coating formed by applying a 0.5% or less silicone solution thereon.

9. The balloon catheter according lb claim 1, wherein the most distal end portion, the distal tapered portion and the balloon straight portion are lubricated, and the most distal end portion and the distal tapered portion have a polyvinylpyrrolidone coating formed by applying a polyvinyl solution thereon and the balloon straight portion has a silicone coating formed by applying a 0.5% or less silicone solution thereon.

10. The balloon catheter according to claim 1, wherein the most distal end portion and the distal tapered portion are not lubricated while the balloon straight portion has a silicone coating formed by applying a 0.5% or less silicone solution thereon.

11. The balloon catheter according to claim 1, wherein the balloon is made of a polyamide elastomer.

12. The balloon catheter according to claim 11, wherein the polyamide elastomer is a polyamide/polyether block copolymer consisting of two or more hard segments of polyamide and two or more soft segments of poiyether.

13. The balloon catheter according to claim 12, wherein the polyamide hard segments in the polyamide/polyether block copolymer is a polyamide consisting of C6 or more higher carboxylic acids and C6 or more higher organic diamines, or C6 or more higher aliphatic ω-amino acids, and the polyether soft segments consisting of C2 to C10 diols.

14. The balloon catheter according to claim 11, wherein the polyamide/polyether block copolymer has a Shore D hardness of 60 or more, arid the polyamide hard segments comprise 50% to 95% by weight of the polyamide/polyether block copolymer.

15. The balloon catheter according to claim 1, wherein the shaft comprises, as the flexible distal section, double tubes composed of an inner tube inside an outer tube made of synthetic polymer, and, as the stiff proximal section a single tube made of metallic material, polyimide or polyetherketone and connected with said outer tube.

\* \* \* \* \*